United States Patent [19]

Aebischer et al.

[11] Patent Number: 5,106,627
[45] Date of Patent: Apr. 21, 1992

[54] NEUROLOGICAL THERAPY DEVICES

[75] Inventors: Patrick Aebischer; Shelley R. Winn, both of Providence, R.I.

[73] Assignee: Brown University Research Foundation, Providence, R.I.

[21] Appl. No.: 613,109

[22] Filed: Nov. 14, 1990

Related U.S. Application Data

[60] Division of Ser. No. 369,296, Jun. 21, 1989, which is a continuation-in-part of Ser. No. 121,626, Nov. 17, 1987, Pat. No. 4,892,538.

[51] Int. Cl.$^5$ .................. A61F 2/00; C12N 11/02; A61K 9/22
[52] U.S. Cl. .................. 424/424; 424/422; 424/423; 435/177; 435/180; 435/182; 530/399; 604/890.1; 604/892.1
[58] Field of Search .................. 424/424, 422, 423; 435/177, 178, 180, 181; 530/399; 604/890.1, 892.1

[56] References Cited

U.S. PATENT DOCUMENTS

| | | | |
|---|---|---|---|
| 3,093,831 | 6/1963 | Jordan | 3/1 |
| 4,241,187 | 12/1980 | White | 435/284 |
| 4,352,883 | 10/1982 | Lim | 435/178 |
| 4,378,016 | 5/1983 | Loeb | 128/260 |
| 4,391,909 | 7/1983 | Lim | 435/178 |
| 4,402,694 | 9/1983 | Ash et al. | 604/891 |
| 4,647,536 | 3/1987 | Mosbach et al. | 435/177 |
| 4,686,098 | 8/1987 | Kopchick et al. | 424/424 |
| 4,883,666 | 11/1989 | Sabel et al. | 424/422 |

FOREIGN PATENT DOCUMENTS

| | | |
|---|---|---|
| 0132384 | 1/1985 | European Pat. Off. |
| 0153825 | 9/1985 | European Pat. Off. |
| 0213908 | 3/1987 | European Pat. Off. |
| 0290891 | 11/1988 | European Pat. Off. |
| 88/04092 | 6/1989 | World Int. Prop. O. |

OTHER PUBLICATIONS

Calne et al. (1969), The Lancet (Nov. 8 issue), pp. 973–976.
Calne et al. (1974), British Medical Journal, vol. 4, pp. 442–444.
Langer et al. (1976), Nature, vol. 263, pp. 797–800.
Sun et al. (1977), Diabetes, vol. 26, No. 12, pp. 1136–1139.
Langer (1981), Methods in Enzymology, vol. 73, pp. 57–75.
Björklund et al. (1982), MacMillan Journals Ltd., Nature, vol. 298, pp. 652–654.
Brundin et al. (1985), Experimental Brain Research, vol. 60, pp. 204–208.
Hefti et al. (1985), Brain Research, vol. 348, pp. 283–288.
Olson et al. (1985), Annals of the New York Academy of Sciences, vol. 457, pp. 105–126.
Brundin et al. (1987), Annals of the New York Academy of Sciences, vol. 495, pp. 473–496.
Freed et al. (1987), Annals of the New York Academy of Sciences, vol. 495, pp. 581–597.

(List continued on next page.)

Primary Examiner—Thurman K. Page
Assistant Examiner—G. S. Kishore
Attorney, Agent, or Firm—Thomas J. Engellenner; Ann-Louise Kerner

[57] ABSTRACT

Neurological therapy devices are disclosed for the local and controlled delivery of a neurotransmitter to the brain of a subject suffering from neurotransmitter deficiency or dysfunction. In one embodiment the device includes a biocompatible, implantable, and retrievable polymeric insert including a source of neurotransmitter embedded therein. In another embodiment, the device includes a retrievable source of neurotransmitter including at least one neurotransmitter-secreting cell encapsulated within a semipermeable membrane allowing the diffusion therethrough of the neurotransmitter, and further includes a source of growth factor in close proximity to the neurotransmitter-secreting cells.

33 Claims, 5 Drawing Sheets

OTHER PUBLICATIONS

Kordower et al. (1987), Annals of the New York Academy of Sciences, vol. 495, pp. 606–622.
Morihisa et al. (1987), Annals of the New York Academy of Sciences, vol. 495, pp. 599–605.
Nguyen et al. (1987), Can. J. Physiol. Pharmacol., vol. 65, pp. 823–827.
Sagen et al. (1987), Annals of the New York Academy of Sciences, vol. 495, pp. 306–333.
Freed et al. (1981), Nature, vol. 292, pp. 351–352.
Schwarz et al. (1987), Annals of the New York Academy of Sciences, vol. 495, pp 786–791.
Wells et al. (1987) Annals of the New York Academy of Sciences, vol. 495, pp. 804–806.
Aebischer et al. (1988), Society of Neuroscience (Abstract), vol. 14, p. 1311.
Aebischer et al. (1988), Brain Research, vol. 448, pp. 364–368.
McRae-Degueurce et al. (1988), Neuroscience Letters, vol. 92, pp. 303–309.
Rosenberg et al. (1988), Reports (Dec. 16), pp. 1375–1378.

NEUROLOGICAL THERAPY DEVICES

CROSS-REFERENCE TO RELATED APPLICATION

This is a division of application Ser. No. 369,296, filed June 21, 1989, which is a continuation-in-part of U.S. patent application Ser. No. 121,626 filed Nov. 17, 1987, now a U.S. Pat. No. 4,892,538, issued Nov. 9, 1990, entitled "*In Vivo Delivery of Neurotransmitters by Implanted, Encapsulated Cells*".

BACKGROUND OF THE INVENTION

The technical field of this invention is the treatment of neurological diseases and, in particular, the treatment of neurotransmitterdeficiency and dysfunction diseases.

Neurotransmitters are small molecules (less than 1 kilodalton (kD) molecular weight) which act as chemical means of communication between neurons. They are synthesized by the presynaptic neuron and released into the synaptic space where they then effect receptors on postsynaptic neurons.

Neurotransmitter deficits have been implicated in various neurological diseases. Lack of neurotransmitter-mediated synaptic contact causes neuropathological symptoms, and can also lead to the ultimate destruction of the neurons involved. Recently, it has been discovered and disclosed in commonly-owned U.S. patent application Ser. No. 121,626 now a U.S. Pat. No. 4,892,538 that localized delivery of the relevant neurotransmitter to the target tissue may reverse the symptoms without the need for specific synaptic contact.

For example, paralysis agitans, more commonly known as Parkinson's disease, is characterized by a lack of the neurotransmitter, dopamine, within the striatum of the brain, secondary to the destruction of the dopamine secreting cells of the substantia nigra. Affected subjects demonstrate a stooped posture, stiffness and slowness of movement, and rhythmic tremor of limbs, with dementia being often encountered in very advanced stages of the disease.

These clinical symptoms can be improved by the systemic administration of dopamine precursors such as levodopa (L-dopa)(Calne et al. (1969) Lancet ii:9-73-976), or dopamine agonists such as bromocriptine (Calne et al. (1974) Bri. Med. J. 4:442-444) and (+)-4-propyl-9-hydroxynapthoxacine (de Yebenes et al. (1987) Movement Disorders 2:291-299) both of which are able to cross the blood-brain barrier, and which are converted into dopamine in the brain. Dopamine, itself, cannot be administered systemically because of its inability to cross the blood-brain barrier.

However, a number of drawbacks are incurred when using this type of chemical therapy. For example, other neurological structures which recognize dopamine as a neurotransmitter are also affected. In addition, it becomes difficult to administer the correct drug dosage with time because the "therapeutic window" narrows (i.e., just after administration, the patient is overdosed, exhibiting excessive spontaneous movement; some time thereafter the drug level may become insufficient, causing the patient to again express Parkinsonian symptoms). Furthermore, the limited potency and/or solubility of most available dopamine agonists precludes continuous in vivo infusions as means to reduce motor deficits in Parkinson's disease. Therefore, what is needed is a method of continuous or constitutive delivery of an undegraded, active neurotransmitter to a localized target region deficient in that neurotransmitter.

In an attempt to provide a continuous supply of dopamine and related drugs to the brain at a controlled rate, miniature osmotic pumps have been used. However, limited solubility and stability of dopamine and related drugs, as well as reservoir limitations, have restricted the usefulness of this technology. Controlled sustained release has also been attempted by implanting dopamine encapsulated within bioresorbable microcapsules (McRae-Degueurce et al. (1988) Neurosci. Lett. 92:303-309). However, controlled sustained release of a drug from a bioresorbable polymer relies on bulk surface erosion, for example, due to various hydrolytic events, increasing the likelihood of drug degradation, and rendering predictable release rates difficult.

The implantation of cells capable of constitutively producing the needed neurotransmitter, reportedly in response to environmental needs, has also been attempted. Recently, remedial transplantation of neurotransmitter-secreting tissue has been accomplished using the patient's own tissue so as not to elicit an immune response. For example, dopamine-secreting tissue from the adrenal medulla of patients suffering from Parkinson's disease has been implanted in their striatum with some success. However, this procedure is only used in patients less than 60 years of age, as the adrenal gland of older patients may not contain sufficient dopamine-secreting cells. This restriction limits the usefulness of the procedure as a remedy since the disease most often affects older people.

Furthermore, abdominal surgery performed to excise portions of the adrenal gland poses substantial risks. Moreover, it is not actually known whether it is the dopamine or other "factors" produced by the implanted cells, or the trauma of the surgery, itself, which alleviates the clinical symptoms. In fact, stereotaxic surgery, or the placement of precisely localized lesions in the brain has been practiced in younger, less affected patients without transplantation and this procedure appears to provide similar relief of Parkinsonian symptoms. The procedure is risky, however, and opinions among neurosurgeons still differ as to the best way of making the lesion and what its ideal location should be.

Alternatives to the transplantation of a patient's brain tissue also include the transplantation of either allograft (identical tissue from another of the same species), or xenograft (similar tissue from another of a different species) dopamine-secreting tissue. However, recent studies have shown that although the brain is considered "immuno-privileged", rejection ultimately occurs with both allografts and xenografts. This problem necessitates the co-adminstration of immuno-suppressors, the use of which renders their own set of complications and deleterious side-effects.

Therefore, there exists a need for improved therapies for neurotransmitter-deficiency diseases in general, and in particular, a need for neurological therapy devices which can augment or replace the functions of dysfunctional neurotransmitter-producing areas of the brain without causing excessive trauma. More specifically, there exists a need for a method of providing active, undegraded neurotransmitter to a localized region of the nervous system of a subject deficient in this neurotransmitter, the correct dosage of which will be constitutively delivered over time.

Accordingly, it is an object of the present invention to provide an implantable neurological therapy device useful for the sustained and controlled delivery of a neurotransmitter to a subject, and more particularly, to provide a device which can deliver neurotransmitter to a localized region in the brain of a subject.

It is another object to provide an implantable device that contains and protects neurotransmitter therein from in vivo degradation such that it is delivered to the subject in an active form. Yet another object of the present invention is to provide an implantable device which can deliver an amount of neurotransmitter responsive to in vivo environmental needs. A further object is to provide an implantable, protective cell culture device which is retrievable, and whose contents are renewable with new and/or additional source of neurotransmitter.

SUMMARY OF THE INVENTION

Neurological therapy devices are disclosed for the local and controlled delivery of a neurotransmitter to the brain of a subject suffering from a neurotransmitter deficiency or dysfunction. It has been discovered that various polymeric materials have the ability to protect various "effector-type" substances, such as neurotransmitters and growth factors, from oxidation, hydrolysis, and degradation when such substances are embedded therein. In addition, these polymeric materials have the capacity for sustained release of the embedded substance at a controlled rate. Recently, it has also been discovered that cells encapsulated within a protective semipermeable membrane, and not in direct contact with a target tissue, are capable of producing neurotransmitter or growth factor in response to the needs of the immediate environment (see commonly-owned co-pending U.S. patent application No. 121,626, now a U.S. Pat. No. 4,892,538).

These discoveries have been utilized to develop the neurological therapy devices of the present invention. One such device includes a biocompatible, implantable, and retrievable polymeric insert including a source of neurotransmitter. In preferred embodiments of this device, the source includes a neurotransmitter which has been embedded within the insert. The polymeric insert protects the neurotransmitter embedded therein from oxidation, enzymatic degradation, and hydrolysis. It may take any shape which is conducive for supplying neurotransmitter, and which can be accommodated by the recipient. Preferred shapes include a fiber or rod.

Useful neurotransmitters to be embedded within the insert include gamma aminobutyric acid, serotonin, acetylcholine, norepinephrine, endorphins, enkephalins, and dopamine. Alternatively, precursors, agonists, active analogs, and active fragments of these neurotransmitters (e.g. dopamine precursor L-dopa and dopamine agonist bromocriptine) may be used.

The polymeric insert includes pores having a molecular weight exclusion of from about 1 kD to about 1,000 kD, but preferably from about 25 kD to about 100 kD. In one preferred embodiment, the polymeric insert includes a hydrophobic matrix such as ethylene-vinyl acetate copolymer. In another embodiment, the insert includes a hydrophilic matrix such as a hydrogel. The insert may additionally include an impermeable portion which is preferably provided by an outer coating of a pure polymeric material such as polyurethane or ethylene-vinyl acetate. The impermeable portion can serve to make the insert function as a conduit for neurotransmitter or whatever substance is embedded therein, and can also aid in supplying the substance to a specific anatomical region of the subject.

An alternative neurological device includes a retrievable source of neurotransmitter and a retrievable source of growth factor in close proximity. The source of neurotransmitter includes at least one neurotransmitter-secreting cell encapsulated within a semipermeable membrane allowing the diffusion therethrough of the neurotransmitter.

The term "semipermeable" is used herein to describe biocompatible membranes that allow the diffusion therethrough of molecules having a relatively low molecular weight, while excluding the passage of those having a relatively high molecular weight.

In one embodiment of the invention, the semipermeable membrane of the receptacle contains pores having a molecular weight exclusion of from about 50 kD to about 100 kD. This membrane excludes the passage therethrough of large particles such as those which are capable of degrading the neurotransmitter or injuring the neurotransmitterproducing cells (e.g. viruses, antibodies, complement, and various proteases). The semipermeable membrane can be made of various polymeric compositions such as a polyvinylchloride, polyacrylonitrile, polyvinylidene fluoride, polystyrene, polymethylmethacrylate, polysulfone, and acrylic copolymers.

The neurotransmitter-secreting cell may include any cell which is known, or has been engineered to produce neurotransmitter, or agonists, precursors, active analogs, or active fragments thereof. For example, chromaffin cells of the adrenal medulla, embryonic ventral mesencephalic tissue, and various neuroblastic cell lines such as PC12 function to supply dopamine, and therefore, are preferred for incorporation into the device. In some aspects of the invention, the cell is an allograft (i.e., cells from another of the same species as the subject in which it is to be implanted) or a xenograft (i.e., cells from another of a different species).

The source of growth factor is situated such that it can easily come into contact with the neurotransmitter-secreting cells encapsulated within the semipermeable membrane. The growth factor maintains cell differentiation and/or stimulates the production and secretion of neurotransmitter. In one preferred embodiment, the source of growth factor includes a polymeric insert with growth factor embedded therein. In another preferred embodiment, the source is at least one growth factor-secreting cell encapsulated within a semipermeable membrane allowing the diffusion therethrough of the growth factor. The growth factor is delivered to the neurotransmitter-secreting cells as it leaches from the insert or as it diffuses from the semipermeable membrane after being secreted by the cells therein.

The invention will next be described in connection with certain illustrated embodiments. However, it should be clear that various modifications, additions, and subtractions can be made without departing from the spirit or scope of the invention. For example, the present invention should not be read to require, or be limited to, a particular device shape, material, neurotransmitter, growth factor, or cell line described by way of example or illustration.

BRIEF DESCRIPTION OF THE DRAWINGS

The invention itself can be more fully understood from the following description when read together with the accompanying drawings in which.

DETAILED DESCRIPTION OF THE INVENTION

Neurological therapy devices are disclosed for the constitutive and controlled delivery of a neurotransmitter, a precursor, agonist, active fragment, or active analog thereof to a target region of a subject suffering from a neurological dysfunction.

Figure 1A:
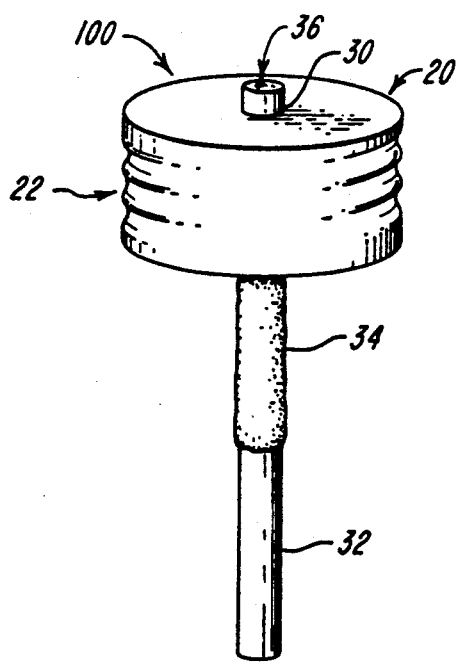
FIGS. 1A-1C are schematic illustrations of an implantable neurological therapy device according to several aspects of the present invention.
Figure 1B:
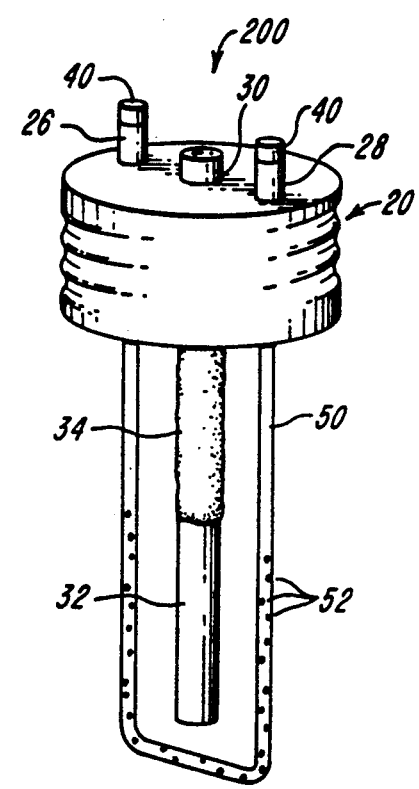
Figure 1C:
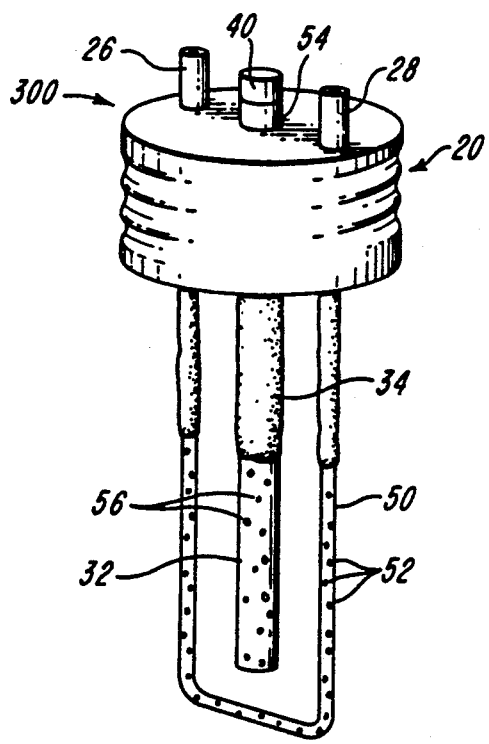

Exemplary embodiments of the neurological therapy device of the present invention are shown in FIGS. 1A-1C in which like reference characters indicate the same or essentially similar elements in the various illustrations. FIG. 1A is a device including an implantable, biocompatible polymeric insert containing the neurotransmitter embedded therein. The device 100 includes a cylindrical cap 20 having grooves 22 on the sides thereof, and a polymeric insert 30 containing neurotransmitter embedded therein. The insert has a permeable portion 32, an impermeable portion 34, and an end 36. Neurotransmitter can diffuse through permeable portion 32, but not through impermeable portion 34.

The insert of the neurotherapy device acts as a conduit for the source of neurotransmitter or growth factor as well as a directed passageway to the anatomical region or specific tissue which requires treatment. In FIG. 1A the insert has the shape of a rod. However, it should be appreciated that the insert may have any shape which can accommodate the source of neurotransmitter without causing undue trauma in the subject upon its surgical implantation.

The neurological therapy devices shown in FIGS. 1B and 1C include a source of neurotransmitter and a source of growth factor in close proximity. The device 200 shown in FIG. 1B includes insert 30 which contains growth factor embedded therein, and further includes semipermeable membrane 50 containing neurotransmitter-secreting cells 52 encapsulated therein. Membrane 50 has the form of a U-shaped tube. However, it should be appreciated that the semipermeable membrane may have alternative shapes that will accommodate the cells such as, for example, a hollow rod, sack, or multiple fibers.

U-tube 50 may be loaded with cells through end 26 or 28. Ends 26 and 28 may be reversibly occluded with friction fitted caps 40, or alternatively with an epoxy glue or sutures of a biocompatible and nonresorbable material. In the device 300 shown in FIG. 1C, semipermeable membrane 50 containing neurotransmitter-secreting cells 52 is accompanied by rod-shaped semipermeable membrane 54 containing growth factor-secreting cells 56 encapsulated therein.

The region targeted for implantation of the neurological therapy device is preferably the brain, as it is often the site of many neurological deficiencies and dysfunctions. Devices 100, 200, and 300 can be surgically implanted into the brain such that permeable portion 32 of insert 30, or semipermeable membrane 50 and 54 are in immediate contact with brain tissues and fluids. Once implanted, the cylindrical cap 20 can be permanently secured to the skull, for example, by screwing it in, and further, by applying a glue or a cement such as dental cement to the cap at the junction of the skull and the cap.

In the event that the neurotransmitter or growth factor supply in insert 30 is spent, the insert can be removed and replaced. Retrieval of implanted insert 30 can be accomplished by pulling it out of cap 20, for example, using a pair of forceps after exposing the device. Cap 20 may be located directly under the patient's epithelial tissues. Insert 30 may be replaced with a new insert in the event that additional neurotransmitter therapy is required. Cells encapsulated within semipermeable membrane 54 (FIG. 1C) can also be retrieved if the cells cease to produce neurotransmitter or growth factor, expire, or are no longer needed to correct the neurological dysfunction. Cells in membrane 50 can be replenished by forcing the cells out of end 26 or 28 by pressure or suction using, for example, a hypodermic syringe.

Permeable portion 32 of insert 30 is implanted at or near the target region, while the impermeable portion 34 confines the neurotransmitter or growth factor to within the boundaries of the insert. The permeable portion 32 includes a polymeric material having pores of a particular size (i.e., having a particular molecular weight cut-off) that excludes some molecules from passage therethrough, while permitting the passage of others. In this way, the diffusion of neurotransmitter from the insert to the target region, or growth factor to the neurotransmitterproducing cells, is allowed, while the passage of larger deleterious elements such as viruses, antibodies, complement, and various proteases is effectively barred. For example, inserts with pores having a molecular weight exclusion of from about 1 kD to about 1000 kD are useful, with those having pores with a molecular weight cut off of from about 25 kD to about 100 kD being particularly preferred.

The insert may be composed of any biocompatible material having the desired pore size and being composed of materials which do not limit the activity of the substance embedded therein. Hydrophilic matrices such as hydrogels (e.g., hydroxyethyl methacrylate, polyvinyl alcohol, and polyvinyl pyrrolidone) and hydrophobic matrices such as ethylene vinyl acetate are particularly useful.

The neurological therapy device can provide any neurotransmitter which will satisfy the deficiency or remedy the dysfunction. These include gamma aminobutyric acid, serotonin, acetylcholine, epinephrine, nor epinephrine, dopamine, enkephalins, and endorphins. Alternatively, the device may provide an active analog, active fragment, or active derivative of the neurotransmitter, or may include a precursor, which after processing, provides the same activity as the neurotransmitter in the appropriate in vivo location. The device may further include an agonist of the neurotransmitter.

One way of providing the source of neurotransmitter includes incorporating it into the polymeric insert. The encapsulating material provides a protective environment for substances such as neurotransmitters or cell growth factors embedded therein, while affording sustained release of the substance at a controlled rate therefrom. For instance, the use of polymeric insert composed of hydrophobic matrices reduces neurotransmitter degradation by inhibiting oxidation and hydrolysis of the neurotransmitter encapsulated therein.

An exemplary method for incorporating the effector substance (e.g., neurotransmitter or growth factor) into the insert includes fabricating the polymeric from a mixture or complex of the polymeric material and the substance. For example, a hydrophobic material such as ethylene-vinyl acetate (EVAc) copolymer can be dissolved in a solvent to which a lyophilate of a neurotransmitter such as dopamine can be added. The mixture is agitated and fabricated into the desired shape by extruding it from a melt. Upon cooling of the mixture, a solid polymeric matrix containing neurotransmitter embedded throughout the matrix is formed (see FIG. 6). Contact of the hydrophilic neurotransmitter with the aqueous environment causes the slow leaching of neurotransmitter therefrom, leading to the development of micropores throughout the matrix of the insert.

The concentration of neurotransmitter added to the hydrophobic matrix material is one factor controlling the rate of neurotransmitter release; the more neurotransmitter incorporated, the more rapid the release rate. The particulate size of the neurotransmitter incorporated into the matrix material is another variable; the larger the particle size, the quicker the rate of release.

The release of growth factor from a polymeric insert can be controlled by the amount of carrier protein co-embedded therewith; the more carrier protein incorporated, the higher the rate of grown factor release. However, the ratio of growth factor to carrier protein is dependent on the levels of growth factor that are effective in the physiologic environment within a therapeutic range. A useful carrier protein is one having the ability to readily dissolve while in the matrix, and having the ability to leach from the matrix. Micropores through which growth factor can leach are created in the matrix when the carrier protein is dissolved by the aqueous environment. Such a carrier protein is bovine serum albumin (apparent molecular weight = about 69 kD).

The release rate may also be controlled by the amount of pure, impermeable polymeric material coating the effector substance-embedded insert; the more (or thicker the) coatings, the slower the release rate. Materials such as polyurethane or pure ethylene-vinyl acetate are particularly useful for this purpose.

Alternative methods of incorporating the source of neurotransmitter include the provision of neurotransmitter-producing cells accompanied by a source of growth factor situated in close proximity thereto. In this embodiment, a semipermeable membrane functions as a protective cell culture device for the neurotransmitter-secreting cells. The pores of the membrane should be large enough to enable the exchange of metabolites with body fluids, and to permit the diffusion therethrough of neurotransmitter produced by the cells therein, but are small enough to bar the passage therethrough of larger elements deleterious to the cells. Pores having a molecular weight cut-off of from about 50 kD to 100 kD are particularly useful for this Purpose.

The semipermeable membrane may take any useful form such as a U-tube, hollow fiber, cell sack or container, or microcapsule. Likewise, if the source of growth factor includes growth factorproducing cells, they, too are encapsulated within a membrane allowing for the exchange of metabolites, growth factor production and diffusion, cell maintenance, and growth (limited by the boundary of the membrane). For a further discussion of such devices, see commonly-owned, co-pending U.S. application Ser. No. 121,626, filed Nov. 17, 1987, the disclosure of which is hereby incorporated by reference.

Any cells which secrete the desired neurotransmitter or growth factor may be incorporated into the device. For example, the cells may be any which naturally produce the neurotransmitter, such as neurons. Such cells are useful because they are able to respond to the general environment by producing neurotransmitter as it is needed. The cells can be obtained from a number of sources such as a body organ which normally secretes a particular neurotransmitter in vivo. For example, tissues of the embryonic ventral mesencephalon and adrenal medulla (chromaffin cells) which normally produce dopamine can be used. These tissues may be an allograft, or they may be a xenograft. Alternatively, the cell may be derived from various cultured neuroblastoid cell lines, such as PC12.

In addition, any cell which secretes a precursor, agonist, active analog, or active fragment of a desired neurotransmitter or growth factor having similar neurotransmitter activity can also be used, including, for example, cells which elicit L-dopa, a precursor of dopamine, or bromocriptine, a dopamine agonist.

Further, any cells which have been genetically engineered to express a neurotransmitter or growth factor, or their agonists, precursors, derivatives, analogs, or fragments thereof having similar effector activities are also useful in practicing this invention. Thus, in such an approach, the gene which encodes the neurotransmitter, or its analog of precursor is either isolated from a cell line or constructed by DNA manipulation. The gene can then be incorporated into a plasmid, which, in turn, is transfected into a cell such as a fibroblast for expression. (See, e.g., Maniatis et al., *Molecular Cloning* (1982), for further discussion of cloning vehicles and gene manipulation procedures.) The cells which expresses the neurotransmitter can be grown in vitro until a suitable density is achieved.

Thereafter, the cells from this culture can be loaded into the neurological therapy device by seeding a portion of the already implanted semipermeable membrane via an orifice located at the skin surface. Alternatively, small tissue fragments or culture aggregates may be preloaded into an encapsulating semipermeable membrane which is then implanted within the subject.

Various "growth factors" having the ability to stimulate cell growth, differentiation, and/or neurotransmitter secretion may be co-implanted with the neurotransmitter-secreting cells to insure successful delivery of neurotransmitter to the subject. These growth factors may be specific for a cell type or have a generalized effect on a number of different tissues. In the case of neurotransmitterproducing cells such as neurons, growth factors can act to maintain neurotransmitter production, as well as to promote cell maintenance and growth. Alternatively, growth factors may maintain nerve cells in a differentiated state. Useful cell growth factors include nerve growth factor (NGF), fibroblast growth factor (FGF), platelet-derived growth factor (PDGF), and epidermal growth factor (EGF), among many. In addition, effectors of various membrane receptors such as glutamate and nicotine may also be useful.

The growth factor may be incorporated into the device with the neurotransmitter-producing cells by embedding it within the polymeric matrix of the insert and placing it in the receptacle with the cells. The embedded growth factor leaches slowly from the insert into the receptacle, thereby acting, for example, to maintain the differentiated state of the cells therein such that they continue to produce neurotransmitter. The encapsulating membrane of the cells, if present, poses no hindrance as it is permeable to the growth factor. This insert may be retrieved from the receptacle and replaced as described above.

Alternatively, growth factor-producing cells such as hippocampal cells or fibroblasts engineered to produce NGF (see e.g., Rosenberg et al. (1988) Science 242:1575-1578) may be encapsulated and implanted in proximity to the neurotransmittersecreting cells as described above.

The following non-limiting examples more fully illustrate preferred features of the invention.

EXAMPLE 1

Experimental Model

Young adult (200-225 g) male Sprague-Dawley rats (Charles River Laboratory, Wilmington, MA) were anesthetized by intramuscular injection of an 87/13 mg/kg mixture of ketamine (Ketalar )/ xylazine (Rompun*). Stereotaxic injections of 6-OHDA (12 mg 6-OHDA in 6 μl of 0.9% saline with 0.05 mg/ml of ascorbic acid) were Performed into the anteriomedial region of the substantia nigra (coordinates: −2.9 mm bregma, 2.3 mm lateral and 8.1 mm deep to the dura with the incisor bar set at 5.0 above the intraaural line). Two weeks after the lesion, rotational behavior was assessed under apomorphine (APO) (0.05 mg/kg sc) challenge. Behavior was characterized both in an open field and modified Ungerstedt rotometer essentially as described by Ungerstedt et al. (Brain Res. (1970) 24:485-493). Animals exhibiting more than eight turns/minute over a 40 minute test period were selected for the study. Groups of 3 animals were housed in plastic cages on a 12 hour on-off light cycle, with food and water available ad libitum.

EXAMPLE 2

Intracranial Cannulation

Sixteen animals received intrastriatal devices made of a 9.5 mm long (0.85 mm ID) semipermeable polyvinyl-chloride-acrylic copolymer (AC) tubular inserts with a molecular weight exclusion of 50 kD. The distal end of the insert was occluded with a solution of the same acrylic copolymer. The first 6 mm from the open end of the insert were coated with a polyurethane solution, rendering this portion impermeable, and therefore, limiting fluid exchange to the striatum.

Sterilized therapy devices were inserted stereotaxically into the striatum (+0.3 mm bregma, 2.7 mm lateral to the midline and 8.0 mm deep to the dura). Once implanted, the therapy devices were secured by equidistant placement of 2 bone screws into the skull, Providing anchorage for dental cement. The proximal port was closed with an AC glue. The therapy device remained in vivo for the duration of the study.

The implantation of empty striatal therapy devices did not induce any new neurological deficits in any of the animals. At the time of implantation of the acrylic copolymer inserts, the Proximal cap of the therapy device was hermetically fused to the tube. After cap removal, the device lumen was filled with an acellular clear liquid.

EXAMPLE 3

Dopamine-Releasing Insert Fabrication

Ethylene-vinyl acetate copolymer (EVAc) resin (40% by weight vinyl acetate, Elvax 40w, DuPont, Inc., Wilmington, DE) was washed 20 times in distilled water and 95% ethanol to remove impurities. Purified EVAc was subsequently dissolved in methylene chloride to make a 10% (w/v) solution. Dopamine (Sigma, St. Louis, MO) was ground in a mortar to a fine powder, sieved to 50 μm, and added to the EVAc solution to a final concentration of 20% dopamine to EVAc (w/w). The dopamine/EVAc solution was ultrasonicated for 5 minutes, agitated in a vortex mixer for 15 minutes, and rapidly cooled in liquid nitrogen in order to form a solid matrix with fixed dopamine Particles. The methylene chloride was removed by lyophilization.

Strings with a diameter of 0.5 mm were Pressure extruded at a temperature of 55° C. and sectioned into rods 8 mm long. To retard dopamine release, three coats of 10% EVAc were applied to each rod by repeated immersion resulting in rods with a final diameter of 0.7 mm. The distribution of dopamine particles in the EVAc was analyzed by scanning electron microscopy (AMRay-1000A, Lico, Inc., Bedford, MA).

EXAMPLE 4

In Vitro Release Kinetics

In vitro dopamine release kinetics were studied by placing a 0.7 × 8 mm long rod in 1 ml of 0.9% Physiologic saline with 0.05 mg/ml of ascorbic acid (+) or (−) 20% dopamine incubated in individual wells at 37° C. At daily time-points, the fluid was collected and its concentration measured by high pressure liquid chromatography (HPLC) with an electrochemical detector. The system used included a Model 5700 solvent delivery module and a model 5100A Coulochem multi-electrode electrochemical detector (ESA, Bedford, MA). A 20 μl aliquot of each sample was injected onto the column (CA-HR 80; ESA) with no sample pretreatment. The mobile phase contained 0.05 M $NaPO_4$, 0.2 M EDTA, 212 mg/L heptane sulfonic acid, and 3% methanol, at a pH of 2.6. Total run time was approximately 8 min. The concentration of each compound was determined by comparison with the peak height of serial diluted standards run with each assay. The dopamine detection limit of the chromatographic system used was 50 pg.

The wells were replenished with fresh saline/ascorbate solution after each measurement. Dopamine release was calculated as cumulative percent release.

Figure 2:
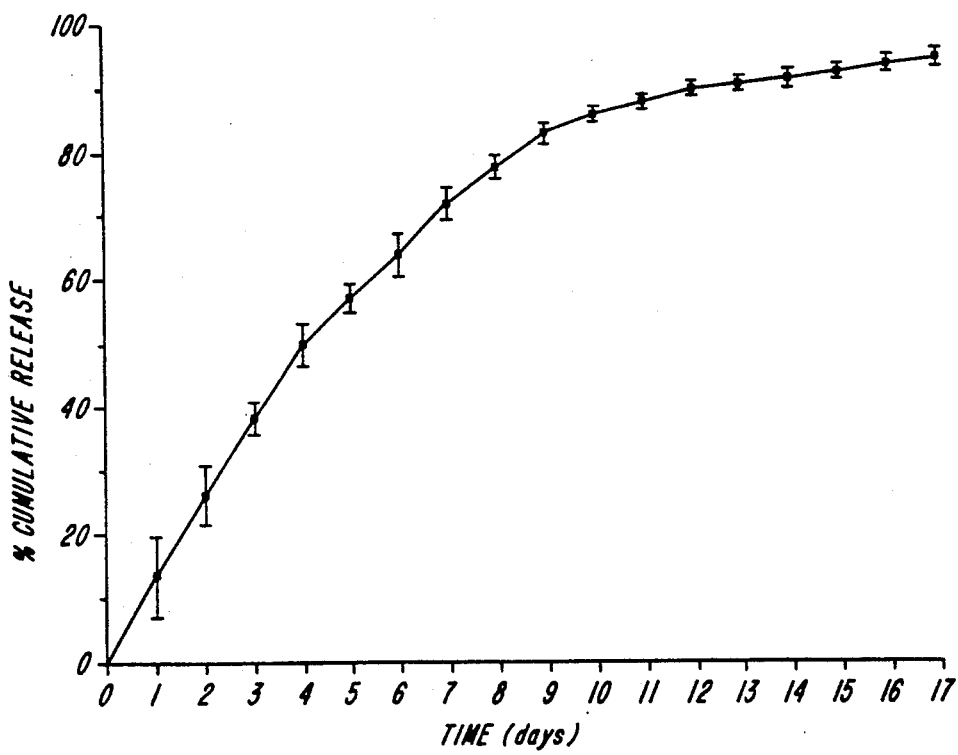
FIG. 2 is a graphic representation of cumulative in vitro release kinetics of eight dopamine/ethylene-vinyl acetate inserts.

FIG. 2 shows the cumulative dopamine release of eight 0.7 × 8 mm 20% dopamine/EVAc rods in 0.9% Physiologic saline with 0.05 mg/ml ascorbic acid at 37° C. over 17 days (FIG. 2). Total dopamine content prior to the release studies amounted to 340 +/− 25 mg per rod.

EXAMPLE 5

Successfully lesioned animals with striatal therapy devices were anesthetized and placed in a stereotaxic apparatus. Following midline incision, the proximal cap on the therapy device was located and excised, and a 20% dopamine/EVAc insert rod was placed in the cap of the device. The proximal end of the device was again sealed with the AC glue. Skin closure was achieved with 6-0 monofilament nylon (Ethicon, Inc., Somerville, NJ).

Rotation behavior was evaluated under apomorphine challenge (0.05 mg/kg) at 7 and 14 days post-dopamine/EVAc loading. The dopamine/EVAc rod was subsequently removed from the receptacle under methoxyfluorane anesthesia at day 14. Behavior was analyzed two and four weeks later.

Figure 3:
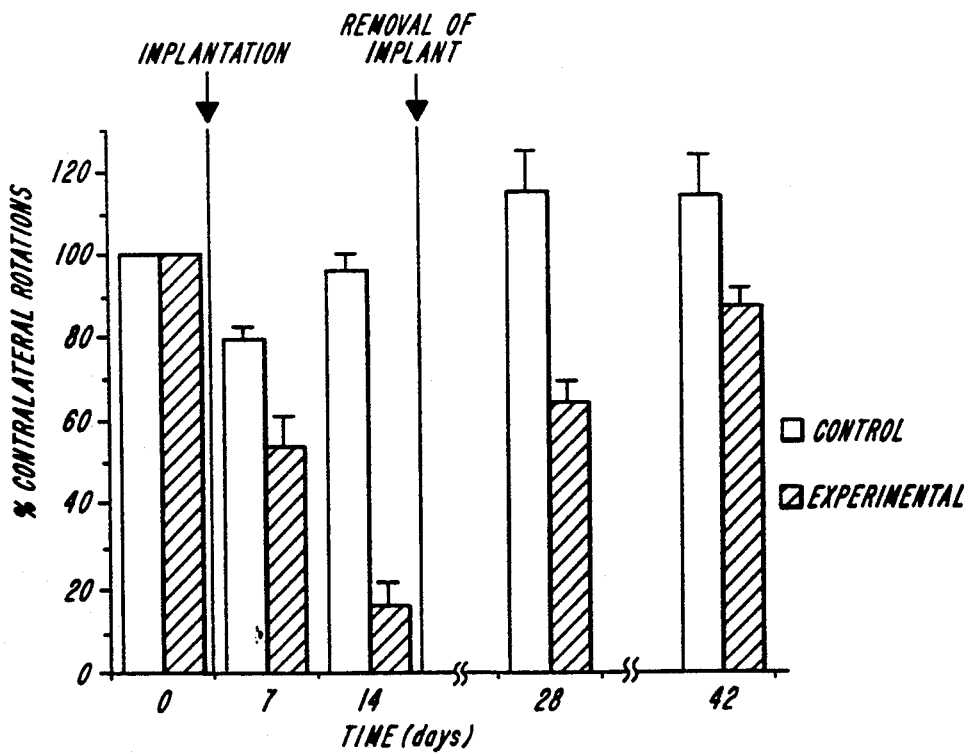
FIG. 3 is a graph demonstrating rotational behavior of animals after the implantation of dopamine-containing neurological therapy devices.

During the first few hours after implantation, the animals receiving dopamine/EVAc inserts spontaneously rotated contralateral to the implant side, whereas animals receiving control inserts did not exhibit such behavior. FIG. 3 summarizes the effect of the APO challenge before, during, and after the implantation of a 20% dopamine/EVAc inserts as compared to control animals, who had received inserts of EVAc alone. Controls showed a slight improvement in rotational behavior 7 days post-implantation with return to preimplantation values at all subsequent time points. Experimental animals displayed a statistically significant decrease in rotational behavior at both 7 and 14 days post-implantation (30.1% at 7 days and 82.6% at 14 days). Two weeks after the removal of the dopamine-release insert, rotational behavior increased again, leaving no statistical difference between the control and the experimental group at 42 days.

EXAMPLE 6

Dopamine Determination

The microdialysis probes used in these experiments were composed of AC semipermeable tubes (600 μm ID, 8 mm long, 50 kD molecular weight exclusion) fabricated by a phase-inversion, dry-jet wet spinning technique (de Yebenes et al. (1987) Movement Disorders 2:291-299). A few hours prior to the experiment, the dialysis probe recovery was determined by placing the probe in a beaker of artificial cerebrospinal fluid (CSF) (150 mmol $Na^+$, 1.4 mmol $Ca^{++}$, 0.8 mmol $Mg^{++}$, 1.0 mmol $PO_4$, 155 mmol $Cl^-$, pH 7.4) containing known concentrations of dopamine, DOPAC, and DHBA at 800 pg/20 ml with 1 mg ascorbic acid in a 100 ml solution. Dopamine concentration was determined by HPLC with an electrochemical detector (EC). The system used included a Model 5700 solvent delivery module (ESA, Bedford, MA) and a model 5100A Coulochem multi-electrode electro-chemical detector (ESA, Bedford, MA). The relative recovery of the dialysate probes was 24–29% at room temperature. Dialysate values are reported as pg per 20 minute collection period.

For in vivo analyses, a dialysis probe was stereotaxically placed in proximity to the previously implanted receptacle in the rat striatum. The animal was anesthetized as previously described. Artificial CSF was pumped through the probe at a flow rate of 2.5 ml/minute throughout the experiment. The dialysate was collected over 20 minute intervals into tubes containing 5 ml 1.1 N perchloric acid. The sample was analyzed immediately by HPLC-EC.

After collecting a number of samples to determine baseline extracellular fluid (ECF) dopamine overflow, a 20% dopamine/EVAc insert was placed in the therapy device. Dialysis samples were collected for 20 minute intervals post-implantation to determine if ECF dopamine levels were affected by the dopamine-releasing insert. Dopamine levels were determined acutely following the implantation of the dopamine-EVAc inserts in 3 animals and 7 days postimplantation in the 3 remaining animals.

A 20 ml aliquot of each sample was injected onto the column (CA-HR 80, ESA) with no sample pretreatment. The mobile phase contained 0.05 M $NaPO_4$, 0.2 M EDTA, 212 mg/L heptane sulfonic acid, and 3% methanol, at pH 2.6. Total run time with resolution of dopamine and DOPAC was approximately 11 minutes. The concentration of each compound was determined by comparison with the Peak height of serial diluted standards run with each assay.

Figure 4:
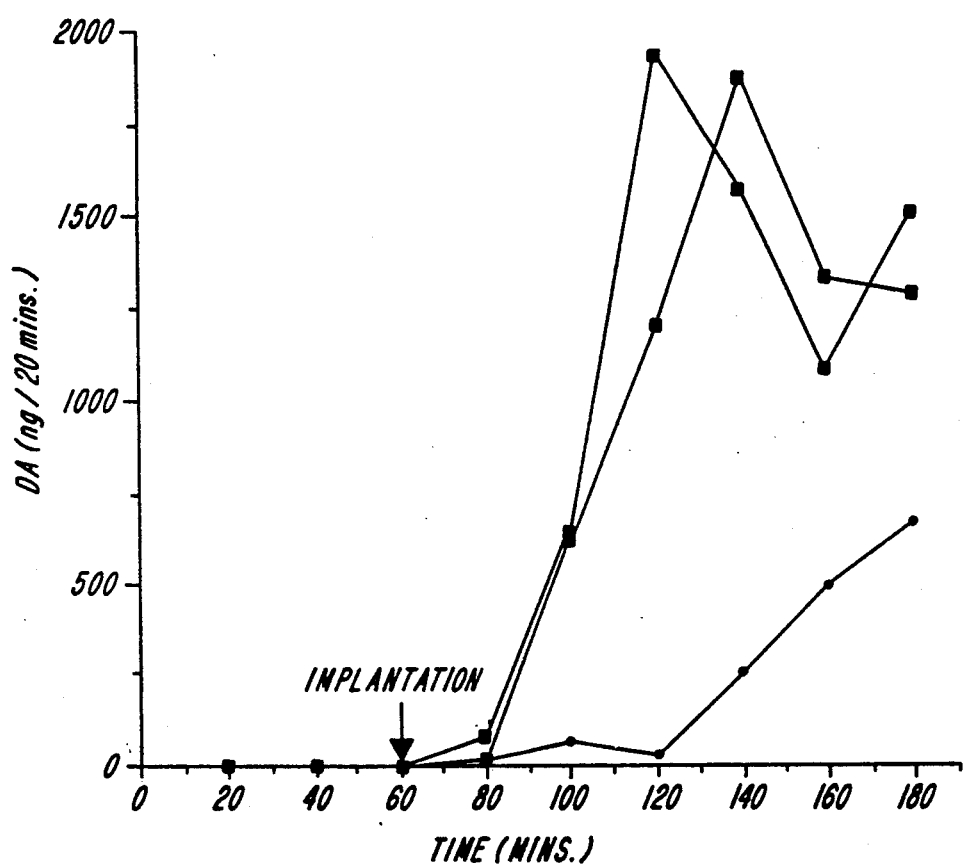
FIG. 4 is a graph showing extracellular dopamine levels in the brain of animals having acutely implanted dopamine-containing neurological therapy devices.
Figure 5:
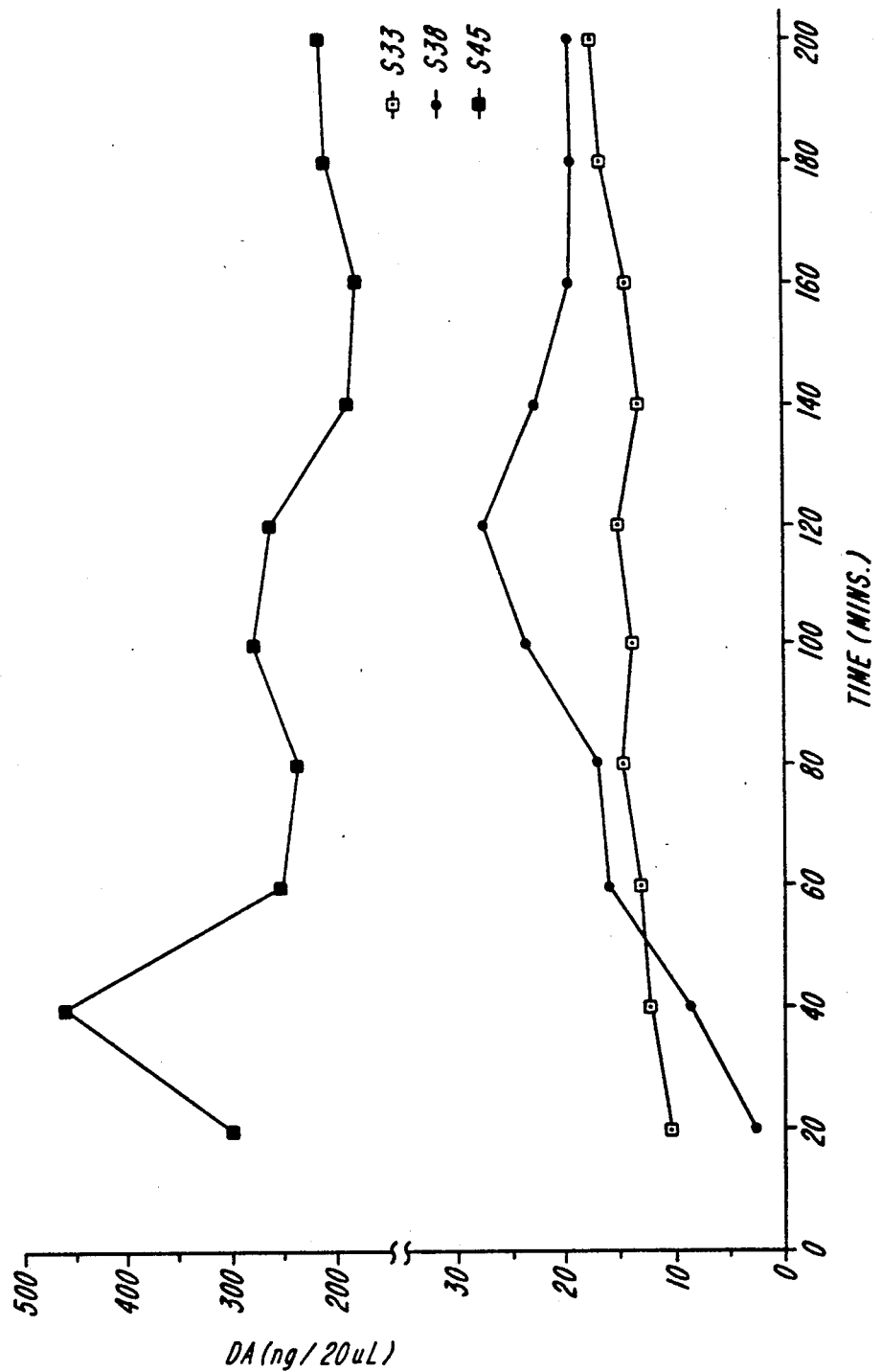
FIG. 5 is a graph showing the level of extracellular dopamine in the brain of 3 animals having an implanted dopamine-containing neurological therapy device 7 days post-implantation.

As shown in FIG. 4, dopamine levels in the extracellular fluid of lesioned striata were consistently undetectable by microdialysis. Twenty minutes after the implantation of a 20% dopaminereleasing EVAc polymeric insert, high levels of dopamine were recovered. The dopamine levels remained elevated throughout the next 80 minutes. In a lesioned striatum studied seven days postimplantation of dopamine/EVAc, the extracellular striatal dopamine concentration in the dialysate was comparable to the levels observed in the acute experiment shown in FIG. 5. Histologically, the microdialysis probes were found to be located 300–500 μm from the devices.

EXAMPLE 7

Histology

Upon completion of the study, deeply anesthetized animals were perfused transcardially. The brain was removed and sections 25 μm thick were cut on a freezing sliding microtome (AO Reichert Model 976 C, Austria), and either picked-up directly on glass slides coated with 3-amino-Propyltriethoxysilane, or immersed directly in Tris buffer. Selected sections were stained for Nissl substance with cresyl violet. Such histological analysis revealed consistent placement of the receptacle within the striatum.

Other sections were processed for immunocytochemical localization of tyrosine hydroxylase (TH) utilizing the avidin-biotin procedure. Brain sections were incubated 2 days at 4° C. in primary antisera to TH (Eugene Tech, Allendale, NJ). Incubations in the secondary antisera and the Avidin-Biotin complex (Vectors Labs, Burlingame, CA) were carried out at room temperature and the peroxidase reaction was developed essentially as described by Winn et al. (J. Biomed. Mater. Res. (1989) 23:31–44). Mounted slides were analyzed with a Zeiss IM 35 interfaced with a morphometric system (CUE-2, Olympus Corp., Lake Success, NY).

At the conclusion of the study, immunohistochemical localization of TH on the substantia nigra and the striatum confirmed greater than 90% destruction of the nigrostratial pathway. No evidence of sprouting surrounding the device was observed.

Figure 6B:
FIG. 6 is a photographic representation of a scanning electron micrograph of a dopamine/copolymer EVAc insert revealing dopamine particles distributed throughout the polymer matrix (A) before implantation, and (B) after implantation.
Figure 6A:

The 20% dopamine/EVAc insert were examined by scanning electron microscopy (SEM) using an AMRay 1000A machine (Lico, Inc., Bedford, MA) prior to and 2 weeks after implantation (FIG. 6). Cross-sectional scanning electron microscopy revealed an even distribution of dopamine particles suspended throughout the polymer matrix (FIG. 6A). Two weeks after incubation in physiologic saline and in vivo, the polymer inserts showed disseminated pits and holes, indicative of dopamine particle dissolution (FIG. 6B).

EXAMPLE 8

Implantation of Dopamine-Producing Cells and Nerve Growth Factor-Releasing Inserts EVAc inserts containing 0.01–0.2% nerve growth factor (NFG) were prepared as described in EXAMPLE 3 except that dopamine is replaced with NGF NGF/EVAc inserts were implanted within the striatal neurotherapy devices of successfully lesioned animals as described in EXAMPLE 5. A suspension of adrenal medulla chromaffin cells was prepared by enzymatic dissociation. The suspension was seeded within the semipermeable membrane by injection of cells in suspension. The proximal end of the device was sealed with AC glue, and skin closure was achieved with 6-0 monofilament nylon (Ethicon, Inc., Somerville, NJ). Rotational behavior was evaluated as described in EXAMPLE 5 at 7, 14, 21, and 28 days Post-NGF/EVAc and cell loading.

Behavioral modification tests and histological analysis after implantation were performed as described in EXAMPLES 5-7, revealing essentially similar results.

What is claimed is:

1. A neurological therapy device for the local and controlled delivery of a neurotransmitter to the brain of a subject, said device comprising:
   a source of neurotransmitter including at least one neurotransmitter-secreting cell encapsulated within a semipermeable membrane, said semipermeable membrane allowing the diffusion therethrough of said neurotransmitter; and
   a source of a growth factor located in close proximity to said encapsulated, neurotransmitter-producing cell for the maintenance of said neurotransmitter-producing cell,
   said source of said growth factor selected from the group consisting of an implantable, biocompatible, polymeric insert containing said growth factor, and at least one growth factor-producing cell encapsulated within a semipermeable membrane that allows the diffusion therethrough of said growth factor,
   said source of neurotransmitter and said source of growth factor including access means for retrieval from the brain.

2. The device of claim 1 wherein said neurotransmitter is selected from the group consisting of gamma aminobutyric acid, serotonin, acetylcholine, norepinephrine, endorphins, enkephalins, dopamine, and precursors, agonists, active analogs, and active fragments of said neurotransmitter.

3. The device of claim 2 wherein said neurotransmitter is the dopamine precursor L-dopa.

4. The device of claim 2 wherein said neurotransmitter is the dopamine agonist bromocriptine.

5. The therapy device of claim 1 wherein said semipermeable membrane within which said neurotransmitter-secreting cell is encapsulated is impermeable to viruses, antibodies, complement, and proteases.

6. The device of claim 1 wherein said semipermeable membrane includes pores having a molecular weight exclusion of from about 50 kD to about 100 kD.

7. The device of claim 1 wherein said semipermeable membrane comprises an acrylic copolymer.

8. The device of claim 1 wherein said neurotransmitter-secreting cell comprises an allograft.

9. The device of claim 1 wherein said neurotransmitter-secreting cell comprises a xenograft.

10. The device of claim 11 wherein said neurotransmitter-secreting cell comprises a neuron.

11. The device of claim 1 wherein said neurotransmitter-secreting cell comprises an adrenal medulla chromaffin cell.

12. The device of claim 1 wherein said neurotransmitter-secreting cell is a neuroblastic PC12 cell.

13. The therapy device of claim 1 wherein said neurotransmitter-secreting cell has been genetically engineered to produce said neurotransmitter.

14. The device of claim 1 wherein said growth factor comprises nerve growth factor.

15. The device of claim 1 wherein said growth factor comprises fibroblast growth factor.

16. The therapy device of claim 1 wherein said source of growth factor comprises an implantable, biocompatible, polymeric insert containing said growth factor.

17. The device of claim 16 wherein said source of growth factor comprises a polymeric insert includes pores having a molecular weight exclusion of from about 1 kD to about 1,000 kD.

18. The device of claim 17 wherein said polymeric insert contains pores having a molecular weight exclusion of about 25 kD to about 100 kD.

19. The device of claim 16 wherein said polymeric insert comprises a hydrophobic matrix.

20. The device of claim 19 wherein said hydrophobic matrix comprises ethylene-vinyl acetate copolymer.

21. The device of claim 16 Wherein said polymeric insert comprises a hydrophilic matrix.

22. The device of claim 21 wherein said hydrophilic matrix comprises a hydrogel.

23. The device of claim 16 wherein said polymeric insert further comprises an outer coating impermeable to said growth factor, said coating covering a portion of said insert for the controlled release of said growth factor from the uncoated portion of said insert.

24. The device of claim 23 wherein said impermeable outer coating comprises polyurethane.

25. The device of claim 23 wherein said outer coating comprises ethylene-vinyl impermeable acetate.

26. The therapy device of claim 1 wherein said source of growth factor comprises at least one growth factor-secreting cell encapsulated within a semipermeable membrane, said membrane allowing the diffusion therethrough of said growth factor.

27. The therapy device of claim 26 wherein said semipermeable membrane within which said growth factor-secreting cell is encapsulated is impermeable to viruses, antibodies, complement, and proteases.

28. The device of claim 26 wherein said semipermeable membrane includes pores having a molecular weight exclusion of from about 50 kD to about 100 kD.

29. The device of claim 26 wherein said semipermeable membrane comprises an acrylic copolymer.

30. The device of claim 26 wherein said growth factor-secreting cell comprises an allograft.

31. The device of claim 26 wherein said growth factor-secreting cell comprises a xenograft.

32. The device of claim 26 wherein said growth factor-secreting cell comprises a murine submaxillary gland cell.

33. The therapy device of claim 26 wherein said growth factor-secreting cell has been genetically engineered to produce said growth factor.

* * * * *